US00PP31798P2

(12) United States Plant Patent
Podaras

(10) Patent No.: US PP31,798 P2
(45) Date of Patent: May 26, 2020

(54) ***BUDDLEIA* PLANT NAMED 'PODARASNGA2'**

(50) Latin Name: ***Buddleia* x *hybrida (Buddleia davidii* x *B. crispa* x *B. alternifolia* x *B. lindleyana)***
Varietal Denomination: PODARASNGA2

(71) Applicant: Early Morning LLC, Greendale, IN (US)

(72) Inventor: Peter Podaras, Tipp City, OH (US)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/501,302

(22) Filed: Mar. 20, 2019

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02; A01H 5/00
See application file for complete search history.

*Primary Examiner* — Kent L Bell
(74) *Attorney, Agent, or Firm* — Barbara Campbell; Cochran Freund & Young LLC

(57) ABSTRACT

A new *Buddleia* plant particularly distinguished by hot magenta colored flowers on very upright shoots, growth is very fastigiate in nature, flower panicles are semi-indeterminate, is disclosed.

2 Drawing Sheets

Genus and species: *Buddleia* x *hybrida* (*Buddleia davidii* x *B. crispa* x *B. alternifolia* x *B. lindleyana*).
Variety denomination: 'PODARASNGA2'.

BACKGROUND OF THE NEW PLANT

The present invention relates to a new and distinct variety of *Buddleia* hereinafter referred to by the variety name 'PODARASNGA2'.

'PODARASNGA2' arose from a controlled cross in Jul. 15, 2014 in Davis, Calif. between an unnamed and unpatented *Buddleia davidii* x *B. crispa* x *B. alternifolia* x *B. lindleyana* female parent, and an unnamed and unpatented *Buddleia davidii* x *B. crispa* x *B. alternifolia* x *B. lindleyana* male parent. Seeds from the cross were sown in April 2015 and 'PODARASNGA2' was selected in August 2015 from the seedling population.

'PODARASNGA2' was first asexually propagated in August 2016 in Wasco, Calif. by softwood cuttings. 'PODARASNGA2' was found to reproduce true to type in successive generations of asexual propagation via softwood cuttings.

SUMMARY

The following are the most outstanding and distinguishing characteristics of this new variety when grown under normal horticultural practices in Wasco, Calif. and Tipp City, Ohio.

1. Hot magenta colored flowers on very upright shoots;
2. Growth is very fastigiate in nature; and
3. Flower panicles are semi-indeterminate.

DESCRIPTION OF THE PHOTOGRAPHS

This new butterfly bush plant is illustrated by the accompanying photographs which shows the plant's overall plant habit including form, fruit, and foliage. The photographs are of a 2-year-old plant taken in July 2018 and grown outdoors in Tipp City, Ohio. The colors shown are as true as can be reasonably obtained by conventional photographic procedures.

DESCRIPTION OF THE NEW VARIETY

Figure 1:
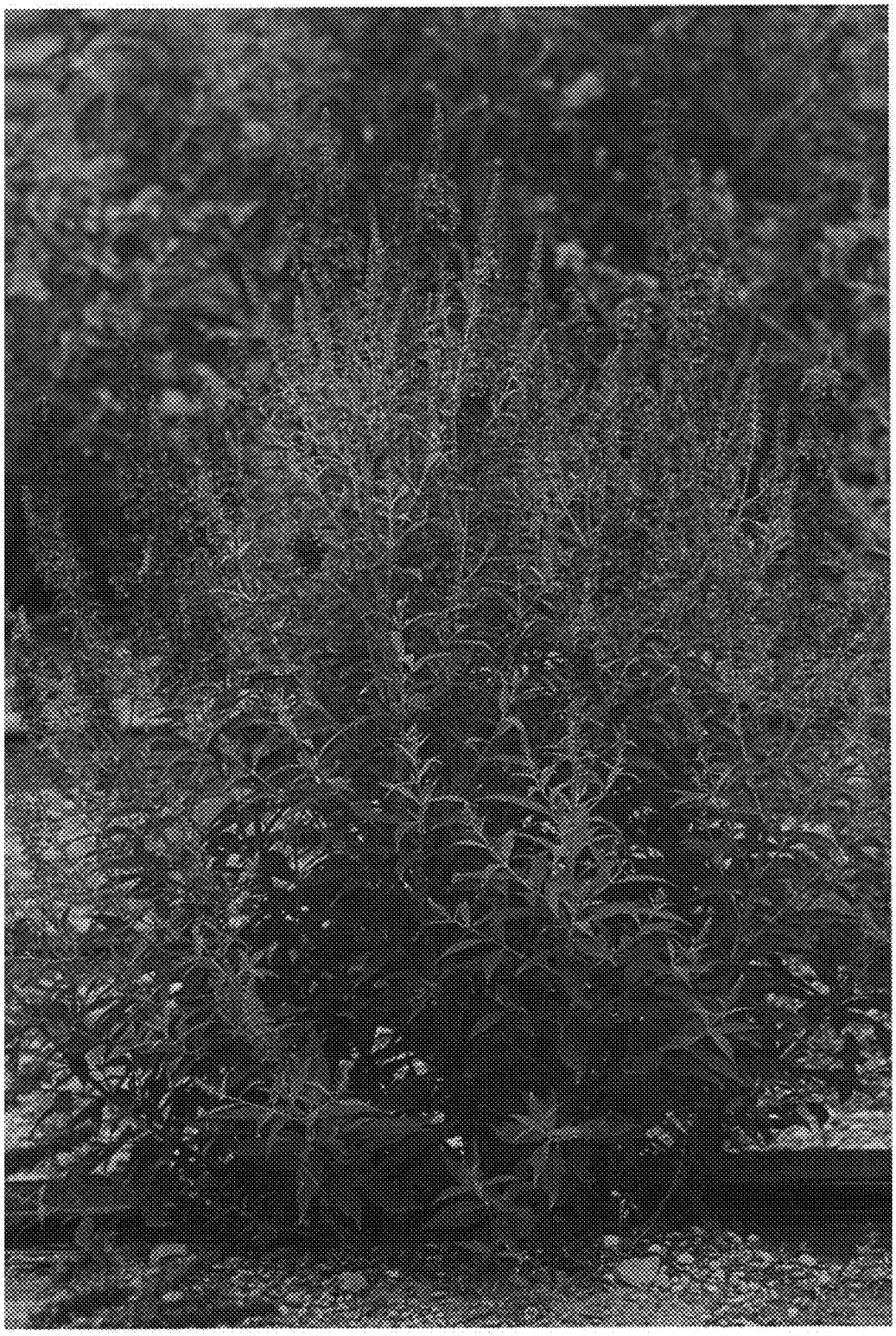
FIG. 1 shows the overall plant habit.
Figure 2:
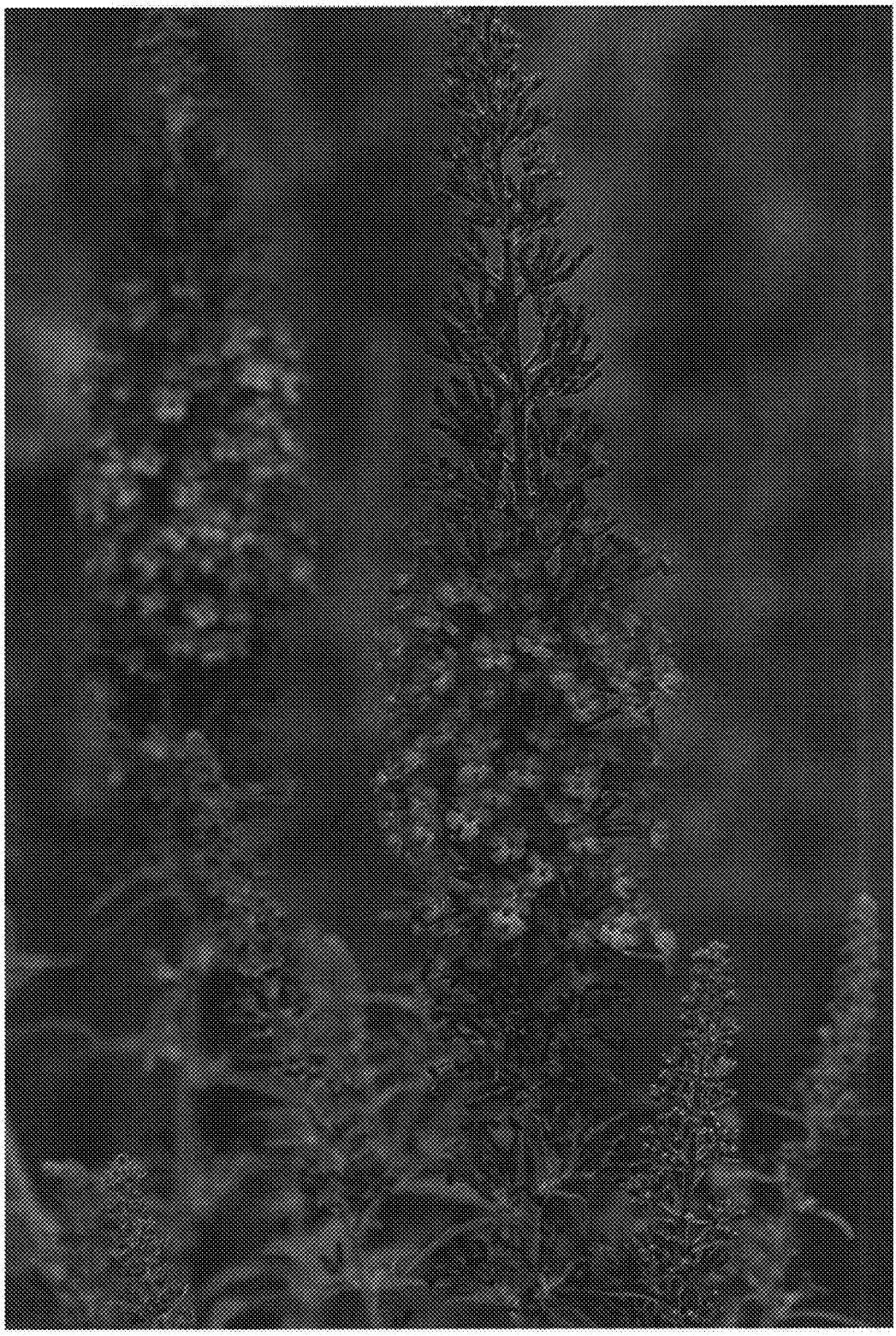
FIG. 2 shows a close-up the foliage, bud, and inflorescences of the plant.

The following detailed descriptions set forth the distinctive characteristics of 'PODARASNGA2'. Measurements were taken from a 2-year-old plant that has been cut back to the ground at the start of its second season of growth in Tipp City, Ohio in September 2019 and grown outdoors. Color references are to The R.H.S. Colour Chart of The Royal Horticultural Society of London (R.H.S.) 2001, Fourth Edition.

Classification:

*Family*.—Scrophulariacace.

*Botanical*.—*Buddleia* x *hybrida* (*Buddleia davidii* x *B. crispa* x *B. alternifolia* x *B. lindleyana*).

*Designation*.—'PODARASNGA2'.

Plant:

*Form*.—Bush/shrub.

*Habit*.—Pyramidal, very vertical branches; dense, heavy branches and fastigiate branching structure.

*Height* (*measured from the top of the soil*).—125 cm.

*Width* (*horizontal plant diameter*).—100 cm.

*Time to produce a finished plant*.—6 to 10 weeks depending on pot size.

*Outdoor plant performance*.—Exceptional.

*Time to initiate and develop roots*.—5 to 7 days using 3,000 ppm IBA.

*Natural flowering season*.—June to frost.
*Root description and habit*.—Fibrous and dense.
*Propagation type*.—Softwood cuttings.

Lateral branches:
*Quantity per plant*.—200 to 250.
*Length*.—Up to 33.0 cm.
*Internode length*.—4.0 cm.
*Diameter* (*from midpoint*).—0.2 cm to 0.4 cm.
*Color*.—RHS 147C but RHS 147B with indumentum rubbed off.
*Strength*.—Flexible, can bend 85 degrees before branches begin to break.
*Texture*.—Slightly pubescent.
*Anthocyanin*.—Present and RHS 165A.

Leaves:
*Quantity of leaves per branch*.—6 to 8.
*Arrangement*.—Opposite.
*Length*.—3.0 cm to 9.1 cm.
*Width*.—0.6 cm to 5.5 cm.
*Shape*.—Lanceolate.
*Apex*.—Acuminate.
*Base*.—Acute.
*Margin*.—Serrate.
*Texture*.—Upper surface: Mostly smooth with some brownish hairs on the veins. Lower surface: Pubescent with appressed stellate hairs.
*Color, immature*.—Upper surface: RHS 191A. Lower surface: RHS 193A.
*Color, mature*.—Upper surface: RHS 137A. Lower surface: RHS 191A.
*Venation pattern*.—Reticulate/anastomosing.
*Petiole*.—Color: Lower part is RHS 146D and upper part is RHS 146C. Length: 1.0 cm. Diameter: 0.2 cm. Texture: Upper part is pubescent, especially in the center, and the lower part has sparser hairs.

*Inflorescence* (*panicle*):
*Appearance*.—Panicles are roughly conical in shape.
*Height*.—8.0 cm to 22.0 cm.
*Width*.—2.5 cm to 4.0 cm.
*Bud*.—Shape: Narrow, conical. Height: 3.0 cm to 5.0 cm. Diameter: 0.5 cm to 1.25 cm.
*Flower*.—Type and habit: Single and salverform flowers arranged in compound terminal panicles; flowers face upright and outward. Fragrance: Present, sweet scent. Lastingness of flowers on the plant: 5 to 10 days. Quantity of flowers per inflorescence: 125 to 360. Depth: 0.8 cm. Diameter: 0.6 cm.
*Petals*.—Arrangement and quantity per flower: Most 4, some 5 arranged in a single whorl with petals fused into a narrow tube. Shape: Reniform with a truncated based because of fusion into the corolla tube. Apex: Rounded. Base: Truncated and fused to corolla tube. Margin: Can be smooth or crenulate on the same flower. Texture: Upper surface: Smooth. Lower surface: Rugose. Color, immature: Upper surface: RHS N81A. Lower surface: RHS N81A. Color, mature: Upper surface: RHS N78. Lower surface: RHS N80.
*Corolla tube*.—Length: 0.8 cm. Width: 0.1 cm. Color: Inner surface: RHS 34B. Outer surface: RHS 42B. Texture: Inner surface: Pilose. Outer surface: Bullate.
*Calyx*.—Arrangement and quantity per flower: Mostly 4 sepals, but 5 may be present, fused at the base and arranged in a single whorl. Sepals: Shape: Fused at ⅛ of the length and the rest of the length. Apex: Apiculate. Base: Obtuse. Margin: Repand. Length: 0.2 cm. Width: 0.05 cm. Texture: Upper surface: Scattered stellate hairs. Lower surface: Smooth. Color: Upper surface: RHS 191B with some reddish-purple highlights of RHS 183D. Lower surface: RHS 141C.
*Peduncle*.—Length: 2.7 cm. Diameter: 0.2 cm. Strength: Strong and pliable. Color: RHS 147C. Texture: Pannose, dense appressed stellate hairs.
*Pedicel*.—Length: 0.1 cm to 0.15 cm. Diameter: 0.05 cm. Color: RHS 147C. Texture: Pannose.

Reproductive organs:
*Stamens*.—Quantity per flower: 4, and rarely, 5. Filament: Length: 0.02 cm. Color: RHS 164D. Anther: Length: 0.125 cm. Color: RHS 155B. Pollen amount: Moderate. Pollen color: RHS 158D.
*Pistil*.—Quantity per flower: One. Length: 0.75 cm. Stigma: Shape: Oblong with retuse apex. Color: RHS 147C. Style: Length: 0.12 cm. Color: RHS 145C. Ovary: Shape: Ovoid. Length: 0.15 cm. Width: 0.75 cm. Color: RHS 146D.

Seeds: Can produce a moderate seed set.

Disease and insect resistance: Very disease resistant, but susceptible to spider mites in the greenhouse.

COMPARISON WITH COMMERCIAL VARIETY

'PODARASNGA2' can be compared to the commercial line 'Podaras #9', also known as 'Flutterby Pink' (U.S. Plant Pat. No. 22,065. 'PODARASNGA2' has hot magenta colored flowers, while 'Podaras #9' has light purple violet colored flowers.

I claim:

1. A new and distinct variety of *Buddleia* plant named 'PODARASNGA2' as illustrated and described herein.

* * * * *